United States Patent
Song

(10) Patent No.: US 6,942,667 B1
(45) Date of Patent: Sep. 13, 2005

(54) BONE ANCHOR

(75) Inventor: John K. Song, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 30 days.

(21) Appl. No.: 10/405,881

(22) Filed: Apr. 2, 2003

Related U.S. Application Data

(60) Provisional application No. 60/369,422, filed on Apr. 2, 2002.

(51) Int. Cl.[7] ............................ A61B 17/56; A61F 2/30
(52) U.S. Cl. ...................................................... 606/72
(58) Field of Search ................................ 606/53, 60, 72, 606/73, 76, 130; 411/337, 366.1, 372.5, 372.6, 411/373, 394, 395, 396, 403, 407, 427; 600/407, 600/417, 425, 426, 429

(56) References Cited

U.S. PATENT DOCUMENTS

| | | | | |
|---|---|---|---|---|
| 3,055,370 A | * | 9/1962 | McKinney et al. | 606/129 |
| 4,790,753 A | * | 12/1988 | Fradera | 433/174 |
| 4,840,617 A | * | 6/1989 | Osterholm | 604/174 |
| 4,998,938 A | * | 3/1991 | Ghajar et al. | 606/130 |
| 5,116,345 A | * | 5/1992 | Jewell et al. | 606/130 |
| 5,125,840 A | * | 6/1992 | Durr et al. | 433/173 |
| 5,394,457 A | | 2/1995 | Leibinger et al. | |
| 5,397,329 A | | 3/1995 | Allen | |
| 5,489,210 A | * | 2/1996 | Hanosh | 433/173 |
| 5,496,326 A | * | 3/1996 | Johnson | 606/88 |
| 5,584,629 A | * | 12/1996 | Bailey et al. | 411/178 |
| 5,807,252 A | * | 9/1998 | Hassfeld et al. | 600/407 |
| 6,073,044 A | * | 6/2000 | Fitzpatrick et al. | 600/426 |
| 6,179,841 B1 | * | 1/2001 | Jackson | 606/73 |
| 6,195,577 B1 | * | 2/2001 | Truwit et al. | 600/411 |
| 6,327,491 B1 | * | 12/2001 | Franklin et al. | 600/429 |
| 6,413,260 B1 | * | 7/2002 | Berrevoets et al. | 606/73 |
| 6,458,134 B1 | * | 10/2002 | Songer et al. | 606/73 |
| 6,459,927 B1 | * | 10/2002 | Franklin et al. | 600/429 |
| 6,499,488 B1 | * | 12/2002 | Hunter et al. | 128/899 |
| 6,517,543 B1 | * | 2/2003 | Berrevoets et al. | 606/73 |
| 6,609,020 B2 | * | 8/2003 | Gill | 600/423 |
| 2003/0176866 A1 | * | 9/2003 | Westerkull | 606/73 |

* cited by examiner

*Primary Examiner*—Kevin Shaver
*Assistant Examiner*—Anuradha Ramana
(74) *Attorney, Agent, or Firm*—Morris, Manning & Martin; Tim Tingkang Xia, Esq.

(57) ABSTRACT

An apparatus and method for fastening a percutaneous medical device to bone is presented, comprising an anchor which comprises an outer threaded segment and an inner cavity comprising an inner threaded segment.

5 Claims, 3 Drawing Sheets

BONE ANCHOR

RELATED APPLICATION

This application claims benefits under 35 U.S.C. §119(e) of co-pending U.S. Provisional Patent Application Ser. No. 60/369,422 filed on Apr. 2, 2002, entitled "Bone Anchor for Use With Implantable Fiducial Markers", the details and disclosure of which is incorporated herein by reference.

BACKGROUND OF THE INVENTION

1. Field of the Invention

The present invention relates to a bone anchor. More particularly, the present invention relates to a low profile bone anchor for fastening percutaneous medical devices to bone.

2. Description of the Prior Art

In certain surgical procedures and medical examination techniques, it is necessary for points or sites to be determined and identified within the body. For instance, stereotactic surgery requires a probe or electrode to be advanced into a patient's brain via a small aperture to a deep-seated brain path or nerve nucleus, while preserving adjacent structures. Likewise, certain imaging medical examination medical procedures, such as Positron Emission Tomography (PET), Roentgen Ray Analysis (X-ray), Computed Tomography (CT), and Nuclear Spin Resonance Tomography (MMR) require identification and location of inner body structures with a high degree of precision.

Conventionally, inner-body locations are pinpointed by percutaneously implanting external fixation pins into the patient's bone, such as his/her skull, to allow attachment of markers or various adaptors or other devices. Each marker contains a substance which provides a contrasting image and the plurality of markers, generally three, can effectively be triangulated to pinpoint inner-body locations. Moreover, the markers can be maintained in position which allows the markers to be positioned in advance of the surgical or examination procedure as well as providing repeatability for follow-on or additional treatments.

Typically, markers, often referred to as fiducial markers, are attached to the body through anchors drilled into bone, such as the skull, in a plurality of locations. The marker can be integral with the anchor, for instance the anchor can be formed of a marker (high contrast) material or, contrariwise, anchors can be installed in the body and then a marker attached to each anchor.

When the anchor system is used, it is possible to attach more than simply a marker to the anchor. For instance, certain devices needed for performing stereotactic surgery can be positioned at the skull using a bone anchor, such as sterotactic frames used to replace older "halo" type devices. Thus, the surgical device is repeatedly and precisely positioned for the procedure.

Conventional bone anchor devices have several drawbacks. First of all, the anchor often protrudes from the skull or other body part to such a degree as to run the risk of snagging or being caught on objects, thus creating the risk of breaking, infection, and causing the anchor to move out of position, in addition to the simple embarrassment and physical discomfort of a protruding anchor. Moreover, attachment methods conventionally used are not as precise as would be desired. Indeed, when a plurality, such as three, anchors is employed, even slight imprecision in each anchor is magnified and exacerbated when the imprecision occurs at each of three anchors.

In one instance of a device suggested for use as a fiducial marker, Leibinger, Leiginger, Felber, and Plangger, in U.S. Pat. No. 5,394,457, disclose a device for marking body sites for medical examinations. The described device consists of an anchor portion slip-fit into bone and a marker then slip-fit into the anchor portion. Clearly, the slip-fitting of the anchor into the bone and the marker into the anchor provide two areas where the fit may not be as precise as may be desired, creating imprecision in location. Although, Leibinger et al., disclose an embodiment where a screw can be inserted through the bottom of the anchor to provide a different anchoring mechanism, there is still a great deal of imprecision inherent in what would then be a three-part system (screw, anchor, marker).

In U.S. Pat. No. 5,397,329, Allen discloses a fiducial implant for a human body. The implant consists of an anchoring portion, which can be threaded, and a marker portion which extends above the bone to which the anchor portion is anchored.

As can be seen, neither of the discussed patents provides the flexibility of an anchor system to which a marker or other device can be removably attached, yet with the degree of precision and low profile sought.

What is desired therefore, is a bone anchor system which provides a high degree of precision in locating points in the center of a body, such as the brain, yet which allows either attachment of a marker or other surgical devices, while still maintaining a low profile with respect to the patient's body.

SUMMARY OF THE INVENTION

The present invention provides a bone anchor system which can be applied to a patient's body to assist in surgical intervention or high precision examination techniques. The inventive bone anchor consists of an outer-threaded segment which can be anchored in a patient's bone, as well as an inner-threaded segment for attachment thereto of a marker or other percutaneous medical device.

Accordingly, it is an object of the present invention to provide a fiducial implant capable of assisting a surgeon or other medical personnel, especially in identifying and locating points within a patient's body.

It is another object of the invention to provide a bone anchor which will assist in identifying points within a patient's body with a desired degree of precision, and repeatability.

It is yet another object of the present invention to provide such a bone anchor which is sufficiently low-profile as to reduce the chances of snagging or other undesirable effects.

These objects and others which will be apparent to the skilled artisan can be achieved by providing an apparatus for fastening a percutaneous medical device to bone, the apparatus including an anchor having an outer threaded segment and an inner cavity with an inner threaded segment. Preferably, the inner cavity further has a polygonal-shaped segment to permit it to be engaged by a device for implanting the anchor into bone.

Advantageously, the anchor also includes a flange capable of limiting the distance the anchor can be implanted in bone. The flange preferably contains a shaped portion capable of being engaged by a device for implanting the anchor into bone. More particularly, the flange can either have a polygonal-shaped inner surface or an outer surface which assumes a polygonal shape.

The anchor can also have a spherical depression sized to receive a localizing guide device useful for guiding a percutaneous medical device into the anchor.

Also in accordance with the present invention, a method is presented for fastening a percutaneous medical device to bone, the method involving implanting in bone the anchor of the present invention. The method includes drilling a pilot hole into the bone in which the anchor is to be implanted, and then implanting the anchor into the bone by engaging the bone by the threaded outer segment of the anchor. The percutaneous medical device can then be fastened to the anchor by engaging the inner threaded segment of the anchor with a threaded segment of the percutaneous medical device.

It is to be understood that both the foregoing general description and the following detailed description present embodiments of the invention and are intended to provide an overview or framework for understanding the nature and character of the invention as it is claimed. The accompanying drawings are included to provide a further understanding of the invention and are incorporated in and constitute a part of this specification. The drawings illustrate various embodiments of the invention and together with the description serve to explain the principles and operation of the invention.

DESCRIPTION OF THE PREFERRED EMBODIMENTS

Figure 1:
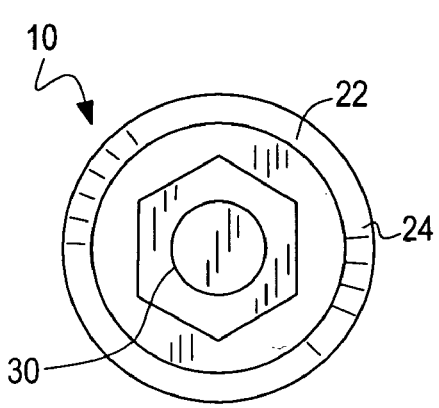
FIG. 1 is a top perspective view of the bone anchor of the present invention.
Figure 2:
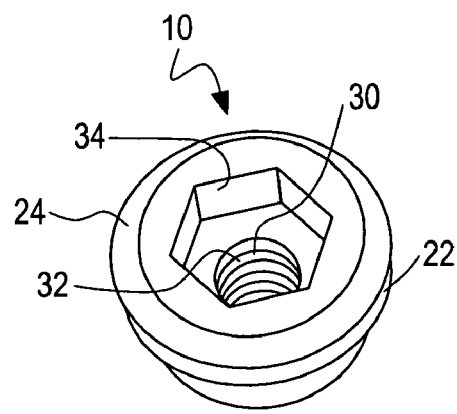
FIG. 2 is a top-plan view of the bone anchor of FIG. 1.
Figure 3:
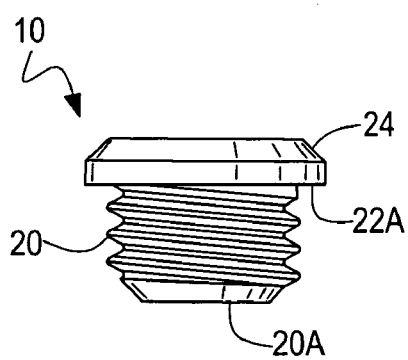
FIG. 3 is a side-plan view of the bone anchor of FIG. 1.
Figure 4:
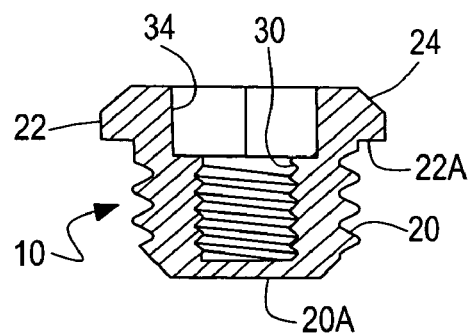
FIG. 4 is a cross-sectional view of the bone anchor of FIG. 3 taken along lines A—A.

Embodiments of the present invention will now be described in greater detail. Like or similar reference numerals will be used whenever possible, although, for the sake clarity, not all reference numbers are necessarily shown in each drawing. Likewise, the invention will be described with respect to a specific orientation and relationship of elements with respect to each other, but it will be recognized by the skilled artisan that other orientations and relationships will be equally applicable. In addition, although the primary use of the inventive bone anchor is for humans, it will be recognized that it is equally applicable to non-human (i.e., animal) uses.

Figure 6:
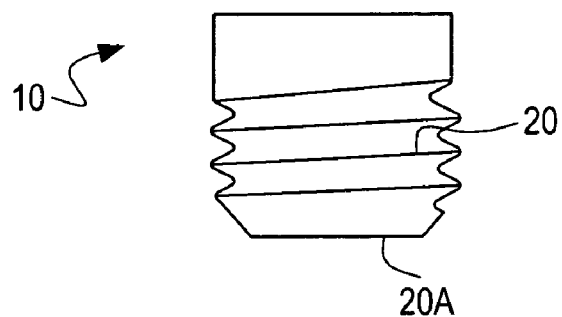
FIG. 6 is a side plan view of an alternate embodiment of a bone anchor in accordance with the present invention.
Figure 7:
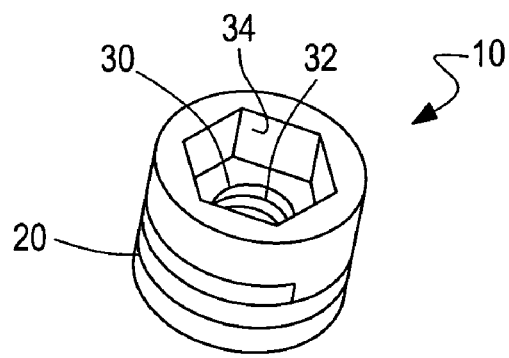
FIG. 7 is a top perspective view of the bone anchor of FIG. 6.
Figure 8:
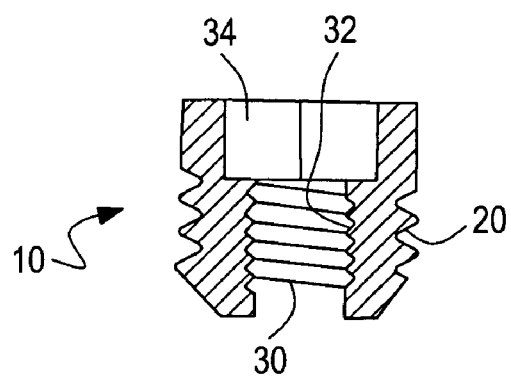
FIG. 8 is a cross-sectional view of the bone anchor of FIG. 6.

A bone anchor in accordance with the present invention is described and denoted by the reference numeral 10. Bone anchor 10 comprises an outer segment 20 having threads formed therein, which can be threaded into a hole drilled in a skull or other bone. As illustrated in FIGS. 1–4, anchor 10 advantageously further comprises a cap or flange portion 22, the bottom surface 22A of which sits against the skull or other bone when anchor 10 is drilled thereinto. Preferably, cap 22 comprises a beveled outer circumferential area 24 to assist in avoiding snags of anchor 10 by the patient. Bone anchor 10 can include a leading point which is shaped to provide self-centering, drilling or tapping features. Alternatively, however, bone anchor 10 can be formed without cap 22, as shown in FIGS. 6–8.

Typically, threaded outer segment 20 of anchor 10 need only be less than about 5 millimeters in diameter at its base 20A to adapt to the conventional size hole drilled in a bone for anchoring. It will be recognized, however, that in practice the diameter of threaded outer segment 20, and of anchor 10 itself, can any diameter needed to engage the hole drilled into the bone in which anchor 10 is to be anchored. As is apparent to the skilled artisan, that diameter should be as small as practicable, for reasons of safety and speed of healing.

Likewise, cap 22 need only extend above threaded outer segment 20 a sufficient distance to provide the required structural stability, and to act as a stop to prevent anchor 10 from being implanted into the bone too far, or, in a worst-case scenario, screwed through the bone and into the tissue on the other side. More particularly, in the case of bone anchor 10 being implanted in a skull, without cap 22, there would be the danger that anchor 10 could be screwed right through the skull and into the brain matter, with potentially harmful results for the patient. Typically, cap 22 need only be on the order of about less than 3 millimeters and typically, less than 2 millimeters in height above threaded outer segment 20 and thus above the bone into which anchor 10 is anchored. In this way, anchor 10 adopts an extremely low profile when implanted in a patient's bone to avoid snagging.

Figure 5:
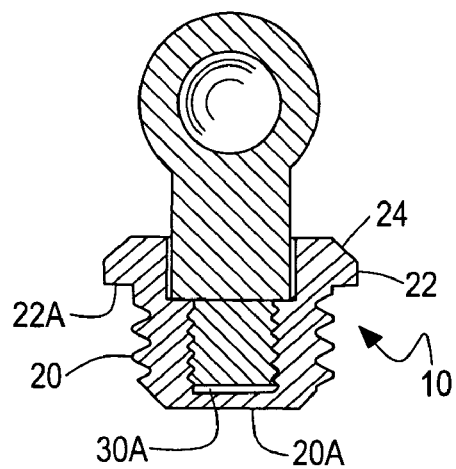
FIG. 5 is a cross-sectional view of the bone anchor of FIG. 1 having a fiducial marker threaded therein.

In addition, as illustrated in FIGS. 1–4, anchor 10 further comprises an internal cavity defined by inner wall 30. In practice, the internal cavity can be "blind," that is, it has a closed bottom, denoted 30A as shown in FIG. 5; alternatively, the internal cavity of anchor 10 can be a through hole, depending on the particular medical procedure to be performed, as shown in FIG. 8. A first segment of the inner cavity defined by wall 30 is inner threaded segment 32, which is threaded to engage a complementary threaded portion of a marker 100 or other surgical device to thereby attach the marker or other surgical device to anchor 10, as illustrated in FIG. 5.

The cavity in anchor 10 defined by wall 30 includes a second segment 34 which adopts a shape useful for engaging anchor 10 in order to implant (i.e., screw) it into the bone to which it is being engaged. Typically, segment 34 adopts a polygonal shape which will allow it to be engaged by an Allen® wrench, hex key or the like and thus permit use of such tool to screw anchor 10 into the bone. Alternatively, other shapes or structures can be formed in cap 22 to permit anchor 10 to be implanted in the bone by use of a screwdriver or other device.

In another embodiment (not shown), the outer edge of cap 22 can assume a polygonal shape to permit anchor to be screwed into the bone by use of a hex head socket, or the like.

Marker 100 or other surgical device can then be attached to anchor 10 by screwing marker 100 into the cavity formed in anchor 10; external threads formed on marker 100 engage the inner threaded segment 32 of anchor 10 to thus securely mount marker 100 to anchor 10. Indeed, the use of threads to anchor the anchor 10 in bone and attach marker 100 to anchor 10 provides a precise mounting method which will permit greater precision in locating an internal site or point in the patient's body.

Anchor 10 (as well as marker 100) can be formed of any material having the desired structural characteristics. Most preferably, the material selected is one which is non-corrosive and which will not react with human tissue, and which can be sterilized. Most preferred, include titanium, polymers such as polytetrafluoroethylene (PTFE) and polysulfon, and ceramics. The material used as the marker within marker 100 can be any material having the desired contrasting characteristics.

In use, a pilot hole is drilled in a patient's skull or other bone in a plurality of locations (preferably three) and anchor 10 screwed into each drilled hole, such that the bottom surface 22A of cap 22 sits against the bone into which anchor 10 is screwed. Marker 100 or other surgical device is then screwed fully into anchor 10, such that its location is precise and repeatable. When not in use, overlying skin can be closed over anchor 10, and a cap placed thereon to avoid tissue obstructing the cavity.

Figure 9:
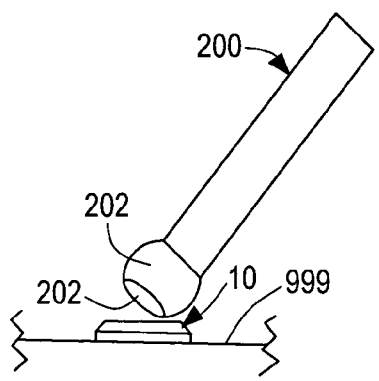
FIG. 9 is a side plan view of the bone anchor in accordance with the present invention implanted in bone, and with a localized guide device being mated therewith.
Figure 10:
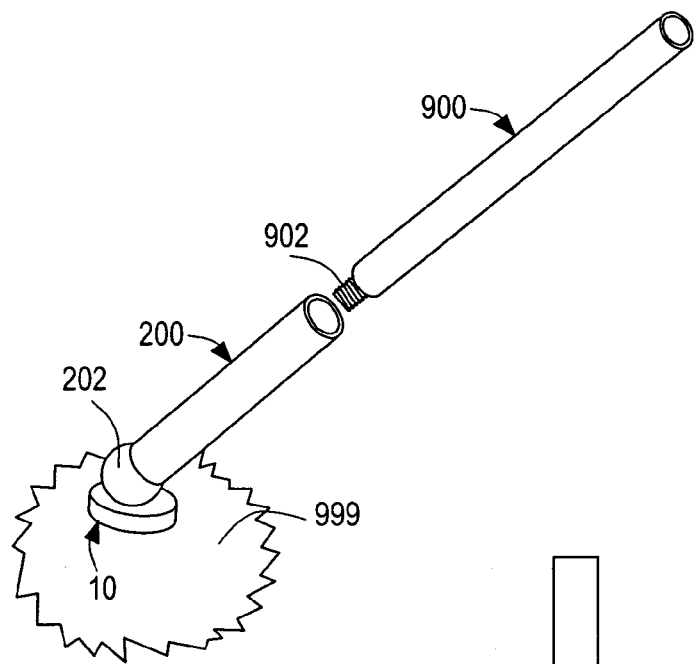
FIG. 10 is a top perspective view of the bone anchor of FIG. 9, having a localized guide device mated therewith.
Figure 11:
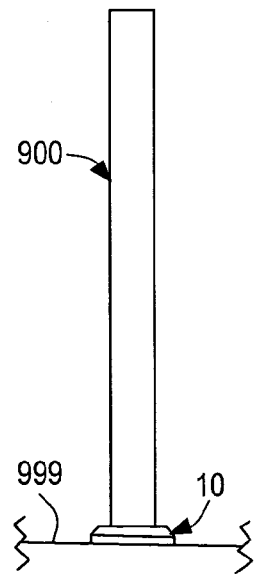
FIG. 11 is a side plan view of the bone anchor of FIG. 9, having a localized guide device mated therewith.
Figure 12:
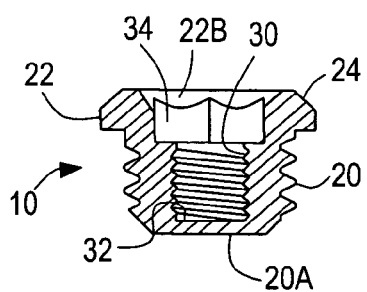
FIG. 12 is a cross-sectional view of another alternate embodiment of a bone anchor in accordance with the present invention, having a spherical depression for mating with a localized guide device.
Figure 13:
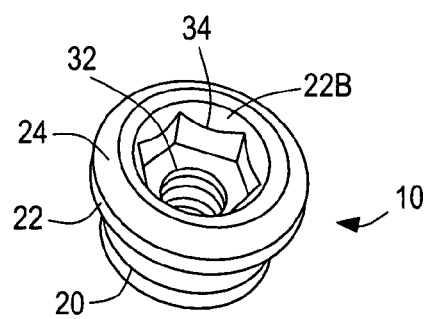
FIG. 13 is a top perspective view of the bone anchor of FIG. 12.

FIGS. 9–13 illustrates how a percutaneous medical device 900 might be placed into a subcutaneously implanted bone anchor 10 using a localizing guide device 200. In FIG. 9, the previously implanted bone anchor 10 is shown having previously been placed into bone 999. The localizing guide device with a spherical end feature 202 is used to locate a mating spherical depression 22B (shown in the embodiments of FIGS. 12 and 13) in anchor 10. Once located, a threaded end 902 of percutaneous medical device 900 (such as marker 100) can be easily guided into the matching threaded inner hole of the bone anchor 10. The localizing guide tube can then be removed leaving the percutaneous medical device 900 in place in anchor 10, as illustrated in FIG. 11.

By use of bone anchor 10 of the present invention, a desirable low profile, precise and repeatable anchoring system, not heretofore seen in the prior art, is provided.

All cited patents and publications referred to in this application are incorporated by reference.

The invention thus being described, it will be apparent that it may be varied in many ways. Such variations are not to be regarded as a departure from the spirit and scope of the present invention and all such modifications as would be apparent as one skilled in the art are intended to be included within the scope of the following claims.

What is claimed is:

1. A system for enabling repeated attachment and detachment of a percutaneous medical device to a precise location of a bone, comprising:
   a subcutaneous bone anchor comprising a body portion, the body portion having an outer engagement surface, in use, for securely embedding within the bone at the precise location, the body portion having a flange adapted to extend above the surface of the bone when the outer engagement surface is embedded within the bone, the flange defining therein a guide depression, the body portion further having a cavity defined therein by an inner threaded segment;
   a percutaneous medical device having a corresponding outer threaded portion adapted for removeable and repeated screwed engagement with the inner threaded segment of the bone anchor; and
   an external guide device having an engagement surface adapted to releasably mate with the guide depression of the bone anchor, the guide device further defining a shaft extending through the engagement surface and adapted for temporary receipt of a portion of the percutaneous medical device to enable proper alignment of the outer threaded portion of the percutaneous medical device with the inner threaded segment of the subcutaneous bone anchor when the engagement surface of the guide device is mated with the guide depression of the subcutaneous bone anchor.

2. The system of claim 1 wherein the guide depression of the subcutaneous bone anchor is spherically shaped to receive the engagement surface of the external guide device.

3. The system of claim 1 wherein the cavity extends into the body portion of the subcutaneous bone anchor away from the guide depression.

4. The system of claim 1 wherein the outer engagement surface of the bone anchor is threaded to enable the bone anchor to be securely screwed into the bone at the precise location.

5. The system of claim 4 wherein the body portion of the bone anchor further comprises a drive surface to enable the subcutaneous bone anchor to be screwed into the bone using a drive tool.

* * * * *